United States Patent [19]

Chrebet

[11] Patent Number: 5,587,322

[45] Date of Patent: Dec. 24, 1996

[54] REPLICA PLATING DEVICE

[75] Inventor: Gary L. Chrebet, Princeton, N.J.

[73] Assignee: ReplicaTech, Inc., Princeton, N.J.

[21] Appl. No.: 344,217

[22] Filed: Nov. 23, 1994

[51] Int. Cl.$^6$ .............................. C12M 1/26; C12M 1/32
[52] U.S. Cl. .................... 435/309.4; 435/30; 435/297.1
[58] Field of Search .................... 435/30, 309.1, 435/309.4, 297.1; 204/415; 73/864, 864.71; 422/99, 101

[56] References Cited

U.S. PATENT DOCUMENTS

| | | | |
|---|---|---|---|
| 3,684,660 | 8/1972 | Kereluk et al. | 195/139 |
| 3,890,202 | 6/1975 | Bergeron | 195/127 |
| 3,897,688 | 8/1975 | Meserol et al. | 195/103.5 |
| 4,325,797 | 4/1982 | Hale et al. | 204/415 |
| 4,397,955 | 8/1983 | Entis et al. | 435/292 |
| 4,634,676 | 1/1987 | Sapatino | 435/294 |
| 4,717,667 | 1/1988 | Provonchee | 435/292 |
| 5,061,621 | 10/1991 | Perlman | 435/30 |

FOREIGN PATENT DOCUMENTS 3254673  11/1991  Japan .............................. 435/292

*Primary Examiner*—William H. Beisner
*Attorney, Agent, or Firm*—Plevy & Associates

[57] ABSTRACT

A device for replica plating of cellular colonies. The device has a solid body with a first region and a first end coupled to a peripheral ridge. A ridge is disposed at the transition from the first region to the peripheral ridge. A sheet of material capable of transferring cellular colonies from one medium to another is placed over the first end and the first region. A locking element defining an aperture passes over the first region and the sheet of material creating a frictional fit which pulls the sheet of material taut over the first end. The sheet of material is compressed between the locking element and the peripheral ridge thereby holding the sheet of material in place.

11 Claims, 3 Drawing Sheets

REPLICA PLATING DEVICE

FIELD OF THE INVENTION

The present invention relates to a replica plating device for obtaining print-replicas of microbial cell colonies or other aggregates from the surface of a culture medium, such as a petri dish, and transferring them to a multiplicity of other media.

BACKGROUND OF THE INVENTION

In microbiological research it is common practice to nurture cell colonies on growth media contained in petri dishes and transfer such cell colonies to other growth media to implement various tests. Laboratory research is facilitated by the replication and identification of the cell colonies under investigation. It is often necessary to clone these cells in order to produce sufficient quantities for a complete investigation of the cells. A process for duplicating cell colonies is widely known as replica plating.

The process of replica plating typically involves a printing-like transfer of a set of colonies from one culture surface to another culture surface or surfaces while maintaining the original pattern of the colonies. The transfer process is commonly performed by contacting cell colonies with a sterile transfer pad and then contact printing these cell colonies onto one or more additional culturing surfaces maintaining their original pattern. It is desirable in the replica plating process to use a device which is easy to operate and provides a large number of high resolution replicates.

Various replica plating tools are found in the prior art. U.S. Pat. No. 5,061,621, to Perlman, entitled REPLICA PLATING DEVICE WITH AN INTEGRAL MARKING ELEMENT, describes a device for replica plating oriented with its cell colony transfer surface face up. The cell colony transfer surface is a fabric laminated with an absorbent blotting material which is bonded to a rigid base. The base is fixed to a flat working surface by an adhesive strip and includes a set of bumper guards positioned on the side wall of the base to prevent contact of the fabric with the inside wall of the culture dish holding the cells to be replicated. This device requires that fabric be rigidly adhered to the base in order to prevent horizontal or vertical movement of the fabric surface. The fabric must be sized such that it covers the base and does not extend beyond the outer circumference of the base. A disadvantage of this device is that the fabric is adhered to base, which prevents easy removal of the fabric for washing and sterilization. Another disadvantage is the device is fixed to a flat work surface possibly requiring the operator to perform the replica plating process at one location and move the replicates to another location for investigation. Perlman does not state whether this device is capable of cleaning, sterilization and reuse or if this is a disposable device intended for only one use which may increase user expenses.

U.S. Pat. No. 4,717,667, to Provonchee, entitled COLONY REPLICATING DEVICE, describes a device that includes a cell colony transfer surface bonded with a water-based latex binder to a resilient backing layer. The cell colony transfer surface must be less resilient than the backing layer. A rigid cap is adhesively fixed onto the resilient backing layer. To use the device, pressure is applied to the cap which is uniformly transmitted to the backing layer and the cell colony transfer surface. A disadvantage of this device is that if the backing layer does not exhibit greater resiliency than the cell colony transfer surface then the force distributed across the cell colony transfer surface may not be even and it will not conform to the host growth medium. Another disadvantage is that the cell colony transfer surface is bonded to the backing layer and does not appear to be easily removed for washing and sterilization, and Provonchee does not state whether this device is capable of cleaning, sterilization or reuse.

U.S. Pat. No. 4,634,676, to Sapatino. entitled REPLICA PLATING DEVICE, describes a cylindrical replica plating device with a hooked skin to maintain the device in a position over the culture container controlling the movement of the device. This device has a layer of thin compressible material attached to the rigid exterior bottom surface of the device. The replica plating technique described includes a replica filter which is placed over the cells in the host medium. The downward movement of the device causes a force to be communicated through the compressible material to the replica filter. A disadvantage of this device is that the cell colonies are printed onto the replica filter, not to another growth medium. Sapatino states that preferably the device is packaged sterile and disposed of after a single use which may increase expenses to the user.

Another typical replica plating tool is disclosed in *Molecular Cloning and Laboratory Manual* by T. Maniatis, published by Cold Spring Harbor Laboratory, 1982, on pages 304–306. The replica plating tool resembles a hand-stamping instrument with a bottom surface and an upwardly extending post for gripping. The bottom surface includes a velvet layer to cushion the pressure of the filter paper against the cell colonies on the culture medium. Similar to the Sapatino device, the velvet layer is for cushioning only and this device only transfers cell colonies from the host medium to the filter paper. A horizontal depth stop is provided to control the depth to which the replica plating tool can penetrate. Adjustment of the horizontal depth stop is awkwardly accomplished. It is questionable as to whether this device insures sterility in the petri dish from which the cell colonies are plate printed.

The prior an demonstrates there is a need for a replica plating device that can be cleaned, sterilized and reused that is easy to operate and produces accurate replicates. The present invention incorporates several features and advantages to overcome the deficiencies of the prior art.

SUMMARY OF THE INVENTION

The present invention relates to an improved replica plating device for transferring cell colonies from a host medium to another medium. The device includes a solid body, a sheet of material for transferring cell colonies from one medium to another medium, and a locking element which slidably engages the solid body.

To use the present invention, a sheet of material is placed over the end of the solid body. The sheet of material should lay flat over the solid body without any ripples or bunching. The locking element is placed over the solid body such that an aperture defined by the locking element aligns over the solid body. The locking element is pressed down over the solid body creating a frictional fit between the aperture defined by the locking element and the sheet of material covering the solid body. This action biases the sheet of material firmly against the solid body. The movement of the locking element progresses to the point where it abuts against a peripheral ridge on the solid body. The peripheral ridge acts as a stop that stops the advancement of the locking element, thereby preventing the sheet of material from being stretched beyond its capacity.

DETAILED DESCRIPTION OF THE FIGURES

Figures 1, 2:
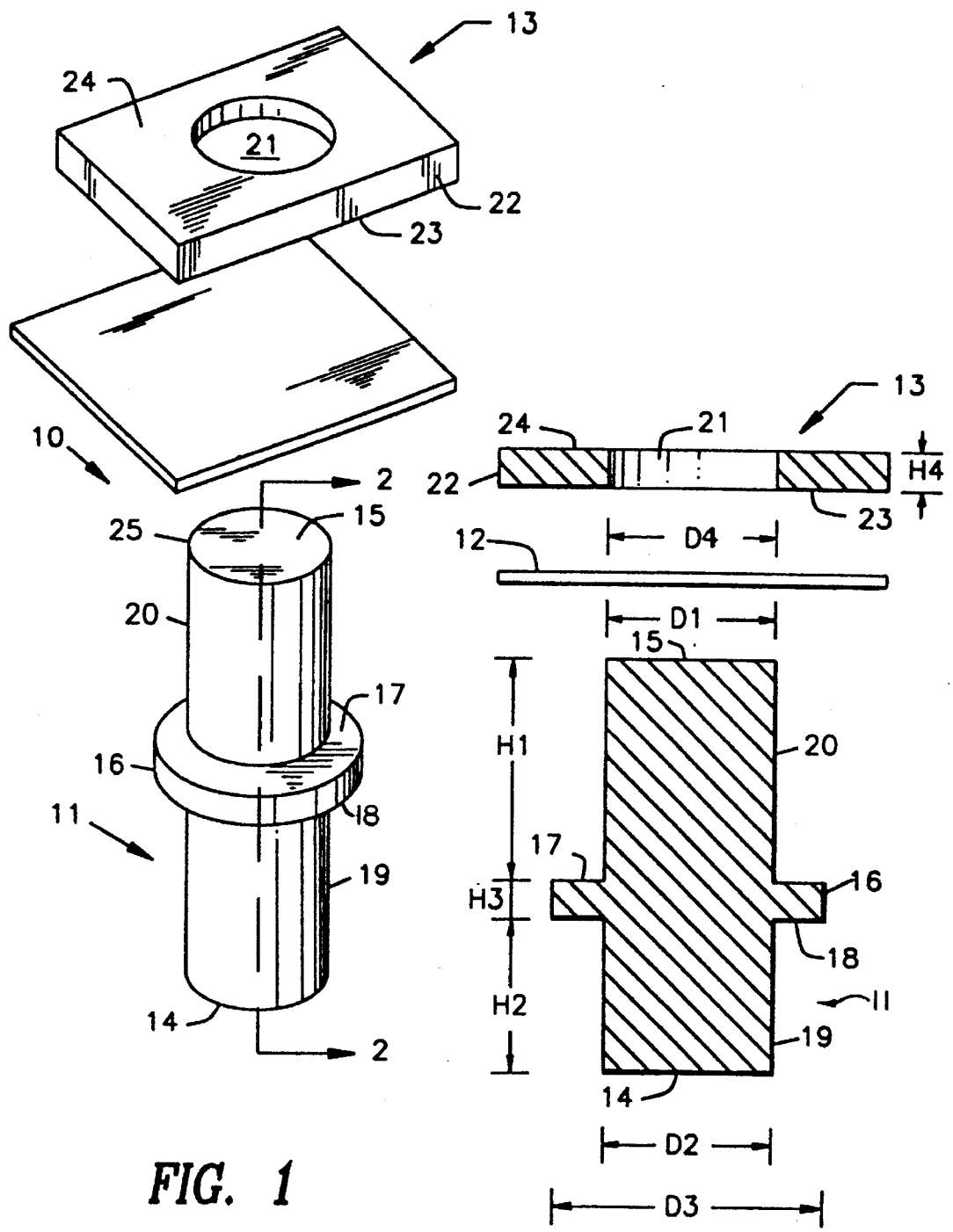
FIG. 1, is an exploded perspective view of a cylindrical embodiment of the present invention.
FIG. 2 is a cross-sectional view of the embodiment of FIG. 1, viewed along section line 2—2.

Referring to FIGS. 1 and 2, there is illustrated one embodiment of the replica plating device 10. The device 10 includes a solid body 11, a sheet of material 12 for transferring cell colonies from one medium to another medium, and a locking element 13 which slidably engages the solid body 11.

The solid body 11 has a cylindrical first region 20 with a circular first end 15. A cylindrical second region 19 with a circular second end 14 is disposed on the opposite side of the solid body 11. A peripheral ridge 16 is coupled between the first region 20 and the second region 19. A first rim 17 is disposed at the transition between the first region 20 and the peripheral ridge 16. A second rim 18 is disposed at the transition between the second region 19 and the peripheral ridge 16. In the preferred embodiment, the solid body 11 is made of a non-porous durable material capable of repeated cleaning and sterilization in an autoclave.

The first region 20 has circular cross-sectional diameter D1. In the preferred embodiment, the cross-sectional diameter D1 is 60 mm, 100 mm or 150 mm to correspond to the sizes of standard round petri dishes. The first region 20 has a height H1 defined by the distance between the first end 15 and the first rim 17. The height H1 of the first region 20 is any length so that it may be inserted far enough into a petri dish to contact the cell colonies deposited on the bottom. The first end 15 of the solid body 11 is substantially planar to maximize the surface area that contacts the cell colonies in a petri dish. The first end 15 has a diameter equal to the cross-sectional diameter D1 of the first region 20. The first end 15 lays in a plane that is at a 90° angle to the side of first region 20. It may be desirable to round the first edge 25 formed where the first end 15 meets the first region 20 to allow for easier insertion into a petri dish and to prevent tearing of the sheet of material 12.

The second region 19 has a circular cross-sectional diameter D2. The cross-sectional diameter D1 of the first region 20 and the cross-sectional diameter D2 of the second region 19 do not have to be equivalent. The second region 19 has a height H2 defined by the distance between the second end 14 and the second rim 18. The height H1 of the first region 20 and the height H2 of the second region 19 do not have to be equivalent. The height H2 of the second region 19 is any length so that it may be inserted far enough into a petri dish to contact the cell colonies deposited on the bottom. It may be desirable to have the height H2 and the cross-sectional diameter D2 of the second region 19 dimensioned for use with a different size petri dish than the first region 20. The second end 14 is substantially planar to maximize the surface area that contacts the cell colonies in a petri dish. The second end 14 has a diameter equal to the cross-sectional diameter D2 of the second region 19. The second end 14 lays in a plane that is at a 90° angle to the side of the second region 19. The diameter D2 of the second end 14 does not have to be identical to the diameter D I of the first end 15. It may be desirable to round the second edge 26 formed where the second end 14 meets the second region 19 to allow for easier insertion into a petri dish and to prevent tearing of the sheet of material 12.

The peripheral ridge 16 is coupled between the first region 20 and the second region 19. The peripheral ridge 16 has circular cross-sectional diameter D3 which is larger than cross-sectional diameter D1 of the first region 20 and the cross-sectional diameter D2 of the second region 19. The cross-sectional diameter D3 of the peripheral ridge 16 must be large enough such that the sheet of material 12 can be held by the locking element 13 against the first rim 17 or the second rim 18. The peripheral ridge 16 has a height H3 defined by the distance between the first rim 17 and the second rim 18. The height H3 of the peripheral ridge 16 is not limited to any specific length. The first rim 17 is located at the transition from first region 20 to the peripheral ridge 16. The first rim 17 is perpendicular to the side of the first region 20 and extends outward from the solid body 11. The second rim 18 is located at the transition from the second region 19 to the peripheral ridge 16. The second rim is perpendicular to the side of the second region 19 and extends outward from the solid body 11.

The sheet of material 12 is preferably a highly absorbent, dense material with a high thread count (1000–2000 pile threads per square inch) and a short pile (less than 1 mm length threads). The sheet of material 12 is used to transfer cell colonies from one medium to a multiplicity of other media with the cell colonies aligned as they were in the original medium. In the preferred embodiment, the sheet of material 12 is reusable and is capable of repeated washing and sterilization.

The locking element 13 secures the sheet of material 12 to the solid body 11. The locking element 13 defines an aperture 21 and has an upper surface 24, a lower surface 23, a side wall 22. In the preferred embodiment, the locking element 13 is composed of a nonporous, durable material that can be repeatedly cleaned, sterilized and reused. The diameter D4 of the aperture 21 is dimensioned such that a frictional fit is created between the aperture 21 and the sheet of material 12 placed over the first region 20. The side wall 22 has a height H4 defined by the upper surface 24 and the lower surface 23. The height H4 of the side wall 22 should be large enough to allow the locking element 13 to withstand the application of the force required to hold the sheet of material 12 securely between the first rim 17 and the lower surface 24. There is no required shape for the perimeter geometry of the locking element 13. In the preferred embodiment, the locking element 13 has a square-shaped perimeter sized such that the user can hold the locking element 13 against the peripheral ridge 16 when using the device 10 to create replicates.

Figures 3, 4:
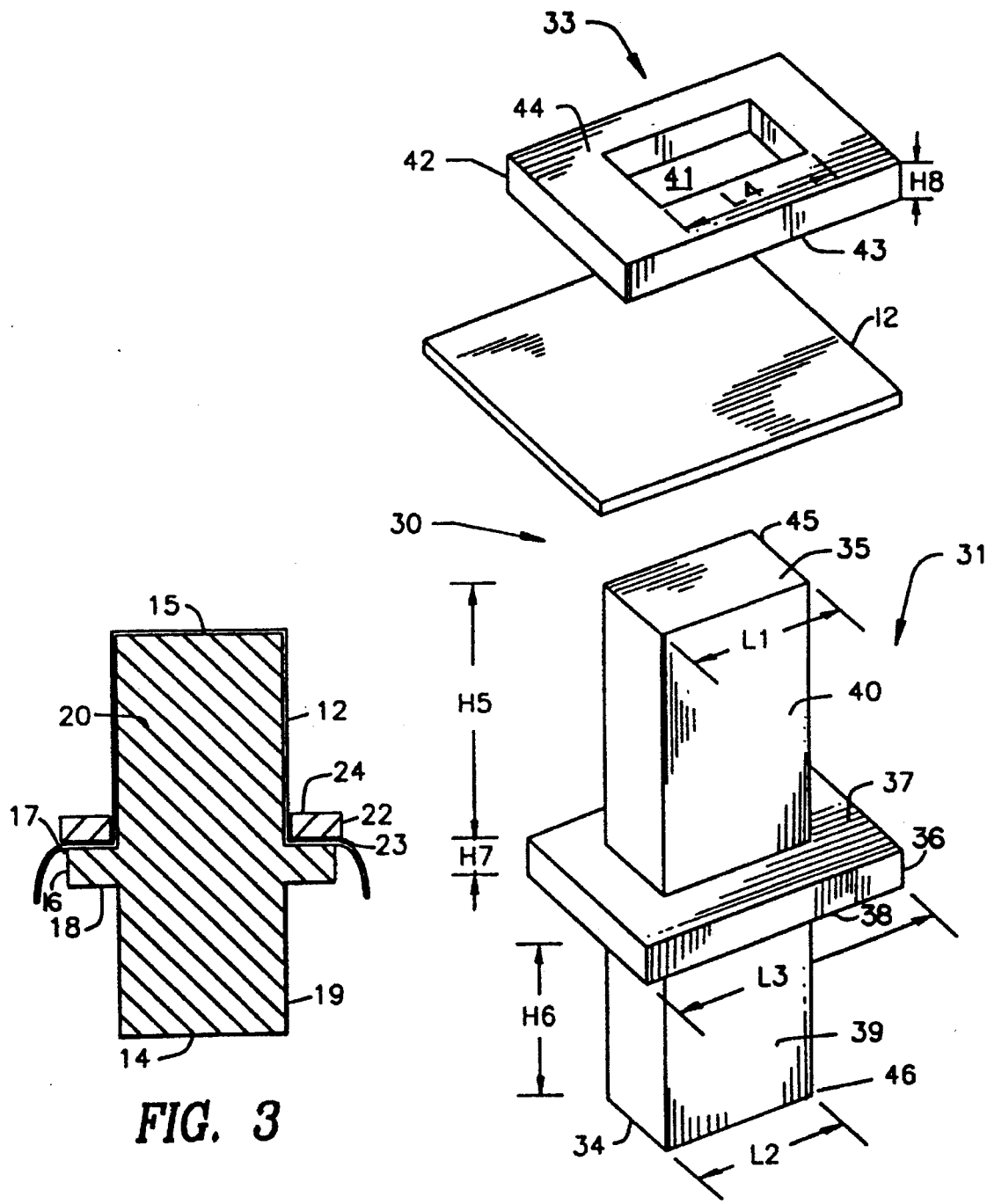
FIG. 3 is a cross-sectional view of the embodiment of FIG. 1 with a fabric engaged by a securing means.
FIG. 4 is a perspective view of a rectangular embodiment of the present invention.

Referring to FIG. 3, there is illustrated the embodiment of FIGS. 1 and 2 after the process of securing the sheet of material 12 to the solid body 11 with the locking element 13 is completed. The process as described below will demonstrate the advantage of this device over those in the prior art because of the ease in preparation for use.

The process begins by placing the sheet of material 12 over the first end 15. The sheet of material 12 should lay flat over the first end 15 without any ripples or bunching. The sheet of material 12 is large enough such that it covers the first end 15, the height H1 of the first region 20 and the first rim 17. The locking element 13 is then placed over the first end 15 such that the aperture 21 and the cross-section of the first end 15 line up having the same center point. The locking element 13 is pressed down over the first region 20 and the sheet of material 12. As the locking element 13 progresses towards the first rim 17, a frictional fit is created between the aperture 21 and the sheet of material 12 covering the first region 20. The movement of the locking element 13 biases the sheet of material 12 holding the sheet of material 12 firmly against the first end 15. The movement of the locking element 13 continues until the lower surface 23 engages the sheet of material 12 against the first rim 17. The locking element 13 compresses the sheet of material 12 between the lower surface 23 and the first rim 17 holding the sheet of material 12 in position during use.

All of the references above are to the first region 20, the first end 15, and the first rim 17. The process is carried out in the same manner when securing the sheet of material 12 over the second region 19 to the second rim 18.

The advantages of the present invention are clearly demonstrated by the ease in which the sheet of material 12 is secured to the solid body 11. The user is not required to guess how much tension to place the sheet of material 12 under when securing it to the solid body 11. The process of sliding the locking element 13 over the sheet of material 12 and the first region 20 holds the sheet of material 12 firmly against the first end 15. This allows for consistent replicates because the sheet of material 12 acting as a cellular colony transfer surface is positioned similarly each time it is secured to the solid body 11. This process also allows for easy removal of the sheet of material 12 from the solid body 11 for cleaning, sterilization and reuse. There are no adhesives necessary for the use of this device. Typical replica plating devices are cylindrical or square and have smooth sides. With a typical replica plating device, a cellular colony transfer material is placed over the device and locked in place with a ring. The ring on has tendency to slip, causing the cellular colony transfer material to move, distorting the replicates. The present invention prevents slippage of the locking element 13 because the locking element 13 is designed to be held against the first rim 17.

Referring to FIG. 4, there is illustrated a second embodiment of a replica plating device 30. The solid body 31 has a first region 40 with a square cross-section and a square first end 35. A second region 39 with a square cross-section and a square second end 34 is disposed on the opposite side of the solid body 31. A peripheral ridge 36 is coupled between the first region 40 and the second region 39. A first rim 37 is disposed at the transition between the first region 40 and the peripheral ridge 36. A second rim 38 is disposed at the transition between the second region 39 and the peripheral ridge 36.

The first region 40 has square cross-section, each side with a length L1. In this embodiment, the length of the side of the square cross-section L1 is 100 mm or 243 mm to correspond to the sizes of standard square petri dishes. The first region 40 has a height H5 defined by the distance between the first end 35 and the first rim 37. The height H5 of the first region 40 is any length so that it may be inserted far enough into a petri dish to contact the cell colonies deposited on the bottom. The first end 35 of the solid body 31 is substantially planar to maximize the surface area that contacts the cell colonies in a petri dish. The first end 35 has a side length equal to the length L1 of the side of the cross-section of the first region 40. The first end 35 lays in a plane that is at a 90° angle to the side of first region 40. It may be desirable to round the first edge 45 formed where the first end 35 meets the first region 40 to allow for easier insertion into a petri dish and to prevent tearing of the sheet of material 12.

The second region 39 has a square cross-section, each side with a length L2. The length L1 of the side of the square defined by the cross-section of the first region 40 and the length L2 of the side of the square defined by the cross-section of the second region 39 do not have to be equivalent. The second region 39 has a height H6 defined by the distance between the second end 34 and the second rim 38. The height H5 of the first region 40 and the height H6 of the second region 39 do not have to be equivalent. The height H6 of the second region 39 is any length long enough so that it may be inserted into a petri dish and contact the cell colonies deposited on the bottom. It may be desirable to have the dimensions of height H6 and the length L2 of the side of the square defined by the cross-section of the second region 39 dimensioned for use with a different size petri dish than the first region 40. The second end 34 is substantially planar to maximize the surface area that contacts the cell colonies in a petri dish. The second end 34 has a side length equal to the length L2 of the side of the cross-section of the second region 39. The second end 34 lays in a plane that is at a 90° angle to the side of the second region 39. The length L2 of the side of the second end 34 does not have to be identical to the length L1 of the side of the first end 35. It may be desirable to round the second edge 46 formed where the second end 34 meets the second region 39 to allow for easier insertion into a petri dish and to prevent tearing of the sheet of material 12.

The peripheral ridge 36 is coupled between the first region 40 and the second region 39. The peripheral ridge 36 has square cross-section, with a side length L3 which is larger than the side length L1 of the cross-section of the first region 40 and the side length L2 of the cross-section of the second region 39. The side length L3 of the cross-section of the peripheral ridge 36 must be large enough such that the sheet of material 12 can be held by the locking element 33 against the first rim 37 or the second rim 38. The peripheral ridge 36 has a height H7 defined by the distance between the first rim 37 and the second rim 38. The height H7 of the peripheral ridge 36 is not limited to any specific length. The first rim 37 is located at the transition from first region 40 to the peripheral ridge 36. The first rim 37 is perpendicular to the side of the first region 40 and extends outward from the solid body 31. The second rim 38 is located at the transition from the second region 39 to the peripheral ridge 36. The second rim is perpendicular to the side of the second region 39 and extends outward from the solid body 31.

The sheet of material 12 in this embodiment has the same properties as in the first embodiment. The locking element 33 secures the sheet of material 12 to the solid body 31. The locking element 33 defines a aperture 41 and has an upper surface 44, a lower surface 43, a side wall 42. The length LA of the sides of the aperture 41 are dimensioned such that a frictional fit is created between the aperture 41 and the sheet of material 12 placed over the first region 40. The side wall 42 has a height H8 defined by the upper surface 44 and the lower surface 43. The height H8 of the side wall 42 should be large enough to allow the locking element 33 to withstand the application of force to hold the sheet of material 12 securely between the first rim 37 and the lower surface 44.

Figure 5:
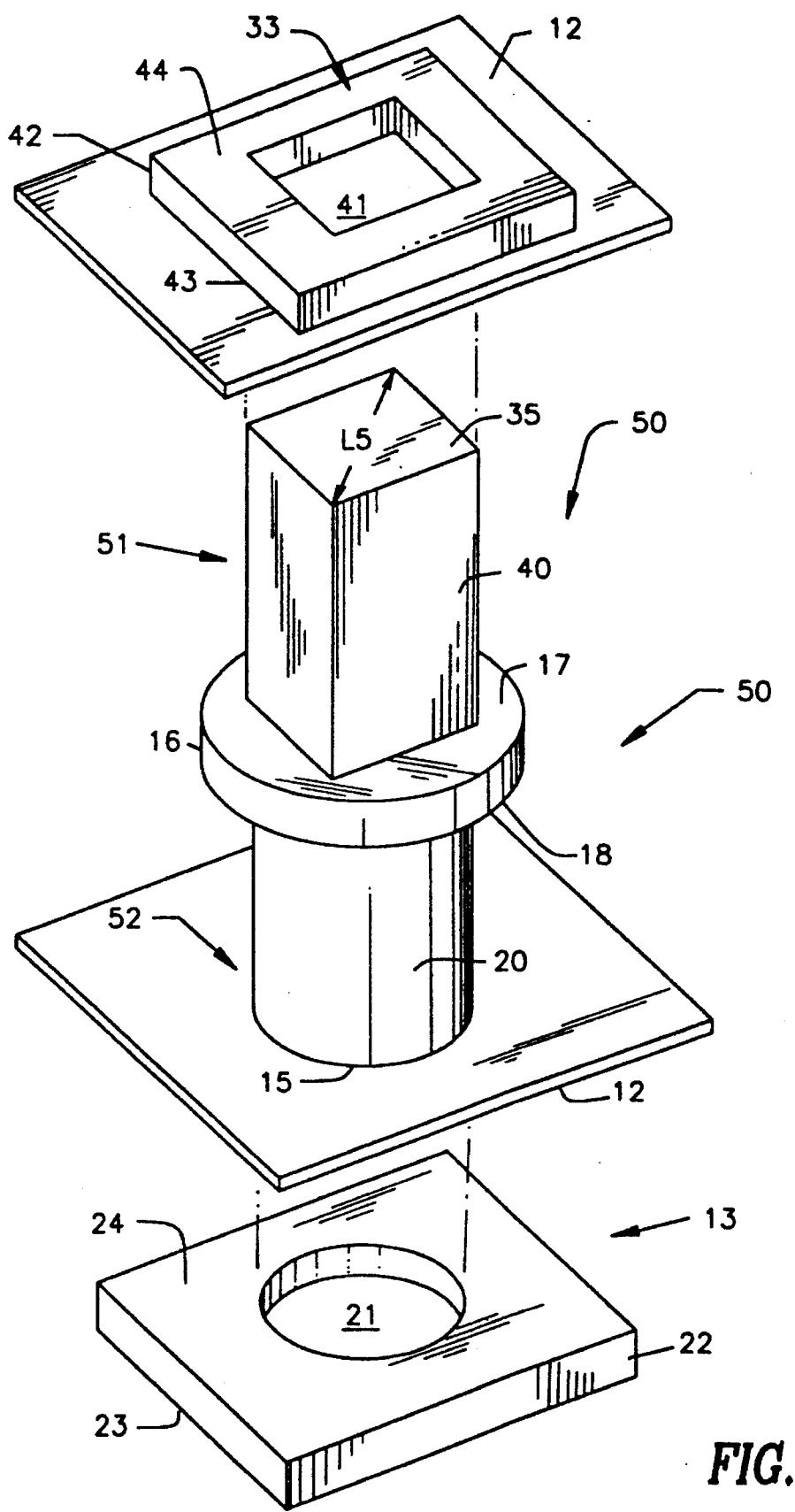
FIG. 5 is a perspective view of the combination of cylindrical and rectangular embodiments.

Referring to FIG. 5, there is illustrated a third embodiment of a replica plating device 50. In this embodiment, the first region 51 has the same dimensions and properties as first region 40 of the square replica plating device 30. The second region 52 has the same dimensions and properties as first region 20 of the circular replica plating device 10. The first region 51 and the second region 52 are coupled to a peripheral ridge 56. In this embodiment, the peripheral ridge 56 has a cross-sectional diameter larger than the diameter D1 first region 51 and the length L5 of the diagonal of the square cross-section of the second region 52. This is so the sheet of material 12 can be held between the locking element 33 and the first rim 17 if the square first region 51 is used or between the locking element 13 and the second rim 18 if the circular second region 52 is used.

In a fourth embodiment, not shown in the FIGS., the solid body has a first end and a second end symmetrically disposed about a longitudinal axis. A sheet of material capable of transferring cellular colonies is positioned such that it covers the first end and a portion of the solid body. In this embodiment, the sheet of material is secured over the first end by a frictional fit created as the locking element slidably engages the solid body covered by the sheet of material.

It should be understood that the embodiments described herein are merely exemplary and that a person skilled in the art may make variations and modifications without departing from the spirit and scope of the invention. For example, the replica plating device may be composed of only two regions, a first for insertion into a petri dish, and the second being the peripheral ridge. A rim is disposed at the transition from the first region to the peripheral ridge to lock the sheet of material onto the replica plating device with the locking element. In another example, the geometric cross-section of the regions described may be other than rectangular or circular. Finally, the peripheral ridge need not be centered relative to the ends of the replica plating device, but offset in either direction depending on the application.

I claim:

1. A device for replica plating having a sheet material capable of transferring cellular colonies from one medium to another medium, comprising:

a rigid support member having a first end and first region terminating at said first end coupled to a peripheral ridge, said rigid support member having a first rim disposed at a point of transition from said first region to said peripheral ridge, said first region having a substantially rectangular cross-sectional geometry with each side of said substantially rectangular cross-sectional geometry having a predetermined length defining the shape of said first end;

said rigid support member having a second end and second region terminating at said second end coupled to said peripheral ridge, said rigid support member having a second rim disposed at a point of transition from said second region to said peripheral ridge, said second region having a substantially circular cross-sectional geometry with a predetermined diameter defining the shape of said second end, said peripheral ridge having a geometric cross section which overlaps said first region creating said first rim and overlaps said second region creating said second rim; and, a locking element defining an aperture through which said sheet of material and laid rigid support member pass, wherein said sheet of material is disposed between said locking element and said first rim and said sheet material is secured over said first end.

2. The device of claim 1, wherein said predetermined diameter of said substantially circular cross-sectional geometry is between 60 mm and 150 mm.

3. The device of claim 2, wherein said predetermined length of said substantially rectangular cross-sectional geometry is between 100 mm and 243 mm.

4. The device of claim 1, wherein said aperture has a shape selected from the group consisting of circular and square.

5. The device of claim 4, wherein said aperture is sized to create a frictional fit with said sheet of material and one of said first region and said second region, when said aperture is placed over one of said first region and said second region.

6. The device of claim 1, wherein said sheet of material is a woven cloth whereby said sheet of material is capable of being washed, sterilized and repeatedly used.

7. The device of claim 1, wherein said sheet of material is disposed between said locking element and one of said first rim and said second rim, and said sheet of material is secured over one of said first end and said second end.

8. A device for replica plating having a sheet material capable of transferring cellular colonies from one medium to another medium, comprising:

a rigid member having a first region having a first cylindrical shape with a first end and a circular cross-section of a predetermined first diameter and a second region having a second cylindrical shape with a second end and a circular cross-section of a predetermined second diameter, said first region and second region seperated by a peripheral ridge extending beyond said first diameter and said second diameter forming a first rim for said first region and a second rim for said second region, said first diameter being different from said second diameter; and, a locking element having a generally square perimeter shape with a circular aperture for inserting over one of said first region and said second region covered with said sheet of material.

9. The device of claim 8, wherein said first diameter is between 60 mm and 150 mm.

10. The device of claim 9, wherein said second diameter is between 60 mm and 150 mm.

11. The device of claim 9, wherein said circular aperature is sized to create a frictional fit with said sheet of material and one of said first region and said second region.

\* \* \* \* \*